United States Patent [19]
Giddings

[11] 4,214,981
[45] Jul. 29, 1980

[54] STERIC FIELD-FLOW FRACTIONATION

[75] Inventor: John C. Giddings, Salt Lake City, Utah

[73] Assignee: University of Utah, Salt Lake City, Utah

[21] Appl. No.: 953,655

[22] Filed: Oct. 23, 1978

[51] Int. Cl.² .............................................. B03B 5/00
[52] U.S. Cl. ........................................ 209/155; 209/1; 210/31 C
[58] Field of Search .................. 209/1, 136, 137, 157, 209/132, 133, 155; 73/23, 23.1, 432 PS; 55/67; 210/519–522, 31 C

[56] References Cited
U.S. PATENT DOCUMENTS

| | | | |
|---|---|---|---|
| 3,272,341 | 9/1966 | Hukki | 209/157 X |
| 3,449,938 | 6/1969 | Giddings | 73/23 |
| 3,865,717 | 2/1975 | Small | 209/1 |
| 3,886,064 | 5/1975 | Kosonen | 209/157 |
| 4,066,536 | 1/1978 | Ball et al. | 209/1 X |

*Primary Examiner*—Ralph J. Hill
*Attorney, Agent, or Firm*—Thorpe, North & Gold

[57] ABSTRACT

A steric field-flow fractionation system including a flow channel adapted for use with a carrier stream of fluid having particles suspended therein and a force field disposed across the flow channel to cause migration of the particles to a restraining wall, thereby forming layers of particles at the restraining wall. The strength of the force field is adjusted sufficiently high to maintain the particles of a given class at the restraining wall such that particle distance from the wall is a function of steric hindrance. Particle displacement by flow along the channel is thereby determined by particle size, permitting fractionation of the particles based on differential migration of the various sizes of particle classes.

15 Claims, 9 Drawing Figures

STERIC FIELD-FLOW FRACTIONATION

This invention was funded in part by a grant from the National Institute of Health, Department of Health, Education and Welfare.

BACKGROUND OF THE INVENTION

This invention relates to a method of field-flow fractionation (FFF), and more particularly to the use of high field gradients to establish particle residence at the wall of a field-flow fractionation system.

FFF, disclosed previously in U.S. Pat. No. 3,449,938, is the descriptive term referring to a broad field of technology developed primarily for separation and characterization of macromolecules and particles. Generally, FFF has demonstrated a capability to deal with extreme ranges of mass, including particles sizes varying from a molecular weight of 600 to particles of almost 1 micrometer in diameter.

As explained in the referenced patent and also in a previous patent application of the present inventor (U.S. patent application Ser. No. 810,835, now U.S. Pat. No. 4,147,621), FFF involves the differentiation and segregation of particles along a flow channel under the influence of a force field applied across the flow channel. The effect of this field, which is usually applied perpendicular to the flow channel, is to force particles of different sizes into equilibrium layers of different effective thickness against a channel wall which operates as a restraining wall with respect to the particles. The thickness of the layers is determined primarily by (1) the interplay between the field-induced forces which tend to compact particles agains the restraining wall and (2) Brownian motion which tends to disperse the particles away from the wall.

Generally, the operation of FFF causes the largest particles to form the most highly compressed layer, located in the channel flow region immediately adjacent the restraining wall. Conceptually, this channel flow is illustrated in FIG. 1 which shows the differential velocities ($V_1$, $V_2$, $V_3$, $V_4$, etc.) of the flow stream across the width of the channel w. It will be noted that the highest velocity ($V_4$) is toward the central region of the channel, with the lowest velocity ($V_1$) occurring at the opposing walls. A field gradient of strength G disposed perpendicular to the flow channel tends to drive the particles toward the restraining wall of the channel as shown.

In all cases of FFF the segregation of particles along the length of the channel occurs because of the differential displacement of particles having different effective layer thickness. In the conventional practice of FFF, the field strength G applied is sufficiently low to permit Brownian motion to displace small particles toward the high velocity central region of the channel, while the larger particles which interact more strongly with the field are retained in layers closer to the wall. It is the differential location of the particles by size along the velocity profile of the channel which causes the fractionation of the particles into particle size groups.

OBJECTS AND SUMMARY OF THE INVENTION

It is an object of the present invention to modify the principles of field-flow fractionation by application of a force sufficiently high to maintain substantially all particles of a given class in contact with or near-contact with the restraining wall of the flow channel.

It is a further object of this invention to define reltionships between channel thickness, particle size, flow rate and other experimental parameter to maximize efficiency of such field-flow fractionation applications.

It is yet another object of this invention to couple a differential sedimentation force with the applied field to adapt the particular field-flow fractionation method for elutriation techniques.

These and other objects are realized in a steric FFF system including a flow channel formed between opposing surfaces of channel walls and a force field disposed across said channel with a field gradient or a vector component thereof in a direction of one of the wall surfaces which operates as a restraining wall. The force field must be of sufficient strength to cause formation of a layer of a given class of particles contained within the flow channel against the restraining wall with the layer thickness being controlled by the steric exclusion of particles from the space occupied by the restraining wall. Such forces may include gravitational, electrical, electromagnetic, photophoretic, centrifugal and fluid cross-flow.

DETAILED DESCRIPTION OF THE INVENTION

Figure 1:
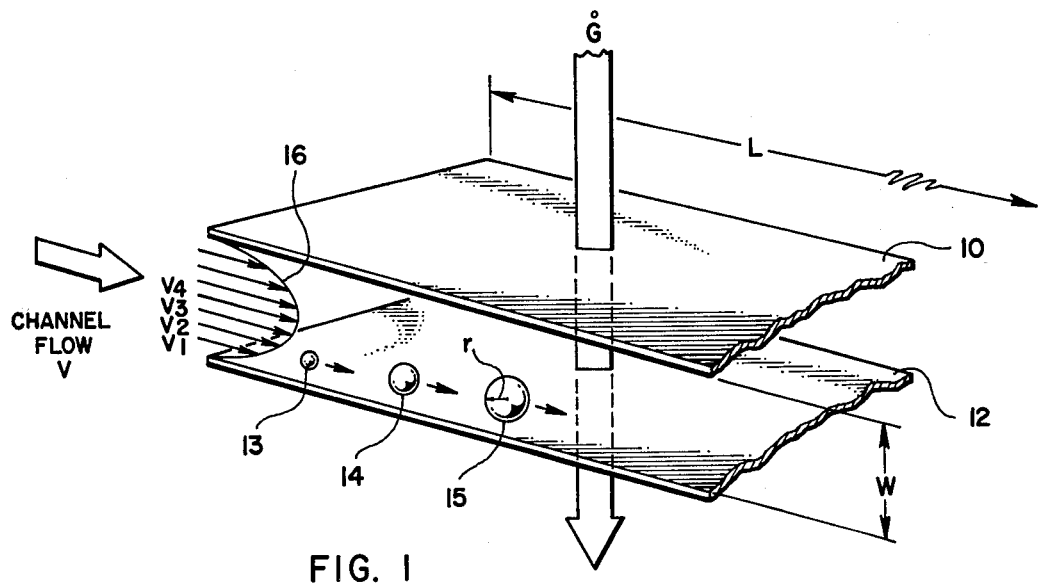
FIG. 1 shows a graphic, perspective view of a FFF flow channel depicting the flow and field gradient applied.

Referring now the drawings:

A graphic illustration of a general FFF device is depicted in FIG. 1, showing flow channel vectors ($V_1$, $V_2$, $V_3$, $V_4$, etc.) representing comparative velocities of stream flow over the cross section of the channel width w. Also shown is the force field of strength $\dot{G}$, representing gravitational force or some other appropriate force applied to particulate matter flowing down the channel. The subject flow channel is formed between two opposing walls 10 and 12 and has stream flow along the length L of the flow channel as indicated by the flow vectors.

As with normal FFF, a field gradient of strength $\dot{G}$ is applied substantially perpendicular to the direction of flow within the channel. In the case of the present invention, the strength of the field is increased to a degree necessary to maintain all the particulate matter against the restraining wall 12 in the FFF device. From this point of view, it can be stated that steric FFF is the high field limit of normal FFF. As the field strength is increased to steric FFF conditions, particles are pushed with increasing firmness into contact or near contact against the restraining wall 12. An optimum steric FFF condition is realized when the mean Brownian displacement of a given class of particles from the wall 12 becomes less than the mean particle radius of a given class of particles. It is therefore apparent that in steric FFF, the radius of the particle becomes determinative as to the rate of differential migration down the flow channel. This term "steric FFF38 reflects the condition that particle layer thickness along the opposing wall 12 is controlled by the steric exclusion of particles from the space occupied by the wall.

For example, particles of increasing size are illustrated within the flow channel as items 13, 14 and 15. In steric FFF, each of these particles is retained as the wall structure 12 of the flow channel by the field gradient $\dot{G}$, representing gravitational or some other force. Because of a difference in radii, each of these respective particle, 13, 14 and 15, projects into a different section of the flow stream 16. Particle 13, for example, projects into and is carried at a stream velocity of approximately $V_2$. Particles 14 and 15, however, will be subject to the increased velocity of $V_3$ and $V_4$ in view of their larger radii. Therefore, large particles (such as particle 15) will migrate along the flow channel in advance of small particles and will emerge from the channel first. It should be noted that this differential migration is an inversion of the normal order of elution of a general FFF system.

A quantitative description reflecting particle movement within the flow channel is given by the retention ratio R which has been defined as particle velocity/mean solvent velocity. J. C. Giddings, *Sep. Sci. and Tech.*, 13 241 (1978). This parameter has been approximated by the limiting expression $$R = (6r/w) + (6l/w) \qquad (1)$$

in which "r" represents the particle radius and "l" represents the average distance from the wall 12 to which the particle is displaced by Brownian motion. While the second of these two terms controls selectivity and separation in normal FFF (where "l" is greater than 0) this term can essentially be eliminated under steric FFF. The appropriate expression for retention ratio in steric FFF would therefore be $$R = (6r/w) \qquad (2)$$

From this proportionality relationship, it can be noted that an increase in particle radius "r" causes a comparable increase in the solute velocity as evidenced by the increase in retention ratio R. It is this differentiation which permits the selectivity in steric FFF.

The practical particle size range of steric FFF is largely determined by the w/r ratio of equation (2). Theoretical estimation suggests that the steric FFFF method functions best within the range of 120 > (w/p) > 12, or within the approximate range of 100 to 10.

Since it is difficult to construct a uniform channel less than 50 micrometers thick (w), the preferred minimum radius (w/r = 100) for a particle will be approximately 0.5 micrometers (diameter equal to one micrometer). By contrast, a 500 micrometer channel is suitable for larger particles (w/r = 10) having a 50 micrometer radius (100 micrometer in diameter). Obviously, thicker channels would extend this large particle capability. In view of these ratios, the preferred steric FFF system particle range would appear to include 1 to 100 micrometers, at the minimum. This range of particle diameters is particularly significant in biology, industry and environmental control studies. Within this range, steric FFF represents a significant advancement in fractionation and characterization methods by improving speed and resolution capability.

As mentioned previously, steric FFF utilizes a similar apparatus to that of conventional FFF. The primary difference involves the relative strength of force applied perpendicular to the flow channel with respect to entrained particles. In the range of particles having diameters from 1 to 100 micrometers, gravity provides sufficient force to establish steric FFF conditions, unless the particles are in a neutrally buoyant medium. This does not mean, however, that other external fields would not be equally effective. Electrical, sedimentation, and other forms of fields or gradients generally applied in FFF may be used to meet the steric FFF field requirement. With gravitational force, the required presence of a uniform field is automatically satisfied and therefore reduces complexity of equipment.

In view of the substantial contact between particles and the surfaces of opposing channel wall 12, new factors with respect to channel construction and flow dynamics are introduced over conventional FFF. The restraining surface of the opposing wall 12 should be inert and flat to reduce tendency of adhesion of particles thereto. Furthermore, surface cracks and indentions must be avoided to prevent traping of small particles.

In addition, flow velocity should be sufficiently high that the viscous forces which drag and roll the particles along the restraining surface of the wall should ordinarily exceed the gravitational forces which pull the particle against the surface. Using such flow velocity will insure that particles are pulled immediately free from any ensnaring influence. These desired high velocities are again in contrast to the lower velocities preferrable in normal FFF.

Particle shape is also a factor to be considered in steric FFF. Spherical particles as illustrated in FIG. 1 can be expected to migrate along the flow channel at remarkable uniform rates. Where particles are of irregular shape, however, more tumbling motion can be expected. In effect, the particles tumble randomly over different extrema at the opposing wall surface to develop a less predictable movement pattern. If, however, flow velocities are maintained high enough to exceed gravitational forces $\dot{G}$ the particle will probably not have time to "settle" between tumbles. It will therefore be carried along at a fairly constant velocity and at a height just skimming the surface. In this case, the radius of the particle defining migration velocity in equation (2) would tend to be that along the longest axis of the particle.

Figure 2:
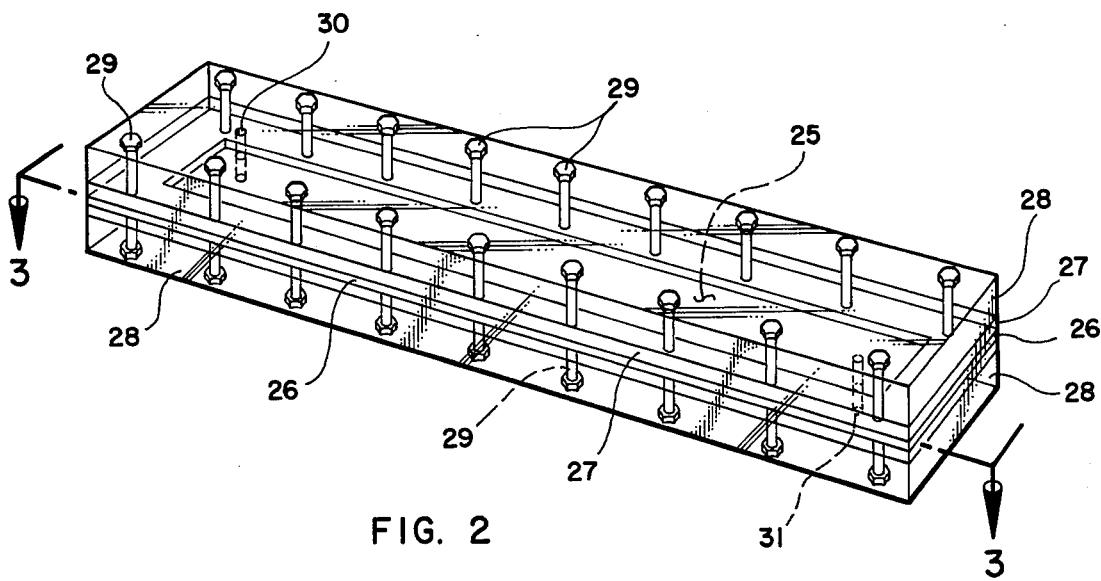
FIG. 2 shows one embodiment of a steric FFF device.
Figure 3:
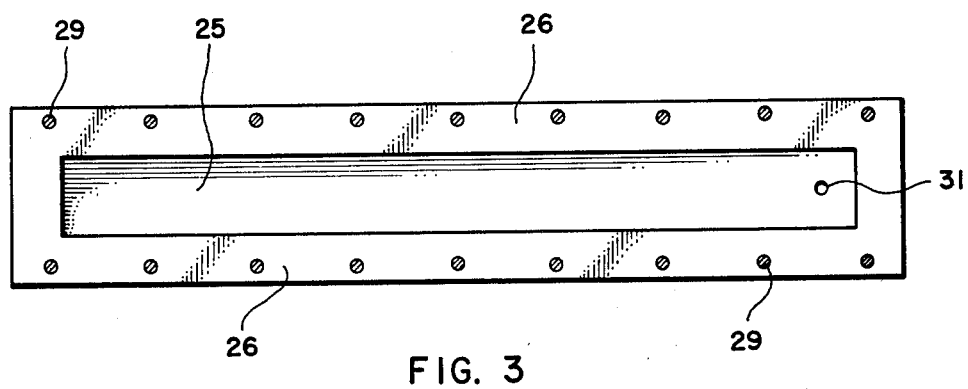
FIG. 3 is a cross section of the steric FFF device of FIG. 2, taken along line 3—3 thereof.

An example of the steric FFF device is shown in FIGS. 2 and 3. The flow channel 25 is formed by the opening of a spacer 26 which is sandwiched between thick pieces of plate glass 27. This combination is clamped between Lucite bars 28 by means of a series of bolts 29. The dimensions of these components as applied in an experimental model of the subject device were as follows:

Mylar spacer (26): 0.127 mm
Plate glass (27): 12.7 mm
Channel dimensions: 10 mm × 860 mm
Channel volume: 1.1 ml Solvent material and particles are injected through an inlet 30, and flow along the length of the channel to an outlet 31. Techniques for injection, detection and collection of samples are the same as disclosed in previous publication, as well as the referenced patent and patent application.

Tests were conducted utilizing glass beads which had been roughly sized by air elutriation in previous experiments. A solvent of 0.05% SDS in distilled water was fed into the channel at the rate of 60 ml/hr by a Chromatronix cheminert metering pump. Samples were collected upon elution and were checked microscopically at 90x and were subsequently photographed. Size distributions were measured by comparing the photographs with a photograph of a microscopic scale standard.

Figure 4A:
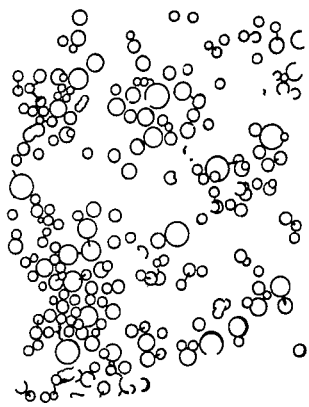
FIG. 4 is a graphic reproduction of a photomicrograph in which (a) is a mixture of glass bead materials and (b) and (c) are the fractionated samples collected at different intervals from a steric FFF system.
Figure 4B:
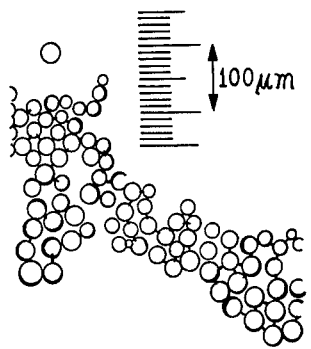
Figure 4C:
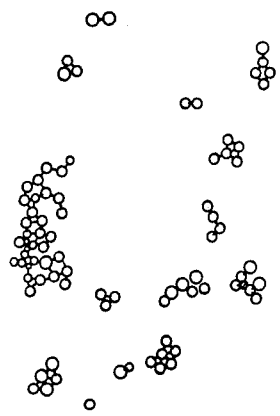

FIG. 4 shows a parent glass bead sample having a broad range of particle sizes which was introduced into the steric FFF system. Photomicrographs of beads collected from two different volume elements of the effluent stream of the apparatus are shown in FIGS. 4(b) and 4(c). Fractionation according to size has been clearly achieved. The respective bead diameters of the two figures are 29±4 micrometers and 19±2 micrometers.

Figure 5:
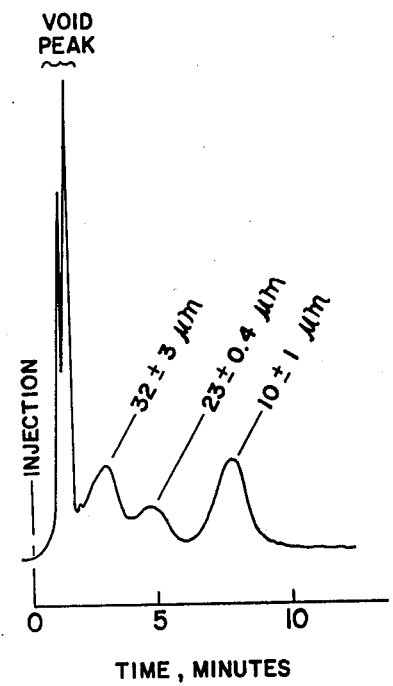
FIG. 5 shows a fractogram of three different sizes of glass beads separated from the sample of FIG. 4.

A second portion of the referenced parent sample of beads was mixed with a second set of smaller beads to provide a trimodal composition. The results of fractionation through the steric FFF device is illustrated in FIG. 5, showing three separate peaks corresponding to the respective sizes of the segregated sample beads.

It is important to note that during normal steric FFF operation, the illustrated apparatus is maintained at a 90° orientation with respect to the applied field. This eliminates a common force component between the flow vectors and the field vector. A second embodiment of the steric FFF method can be achieved by modifying this orientation to a sloping channel, having flow movement opposing a component of the field force vectors.

Figure 6:
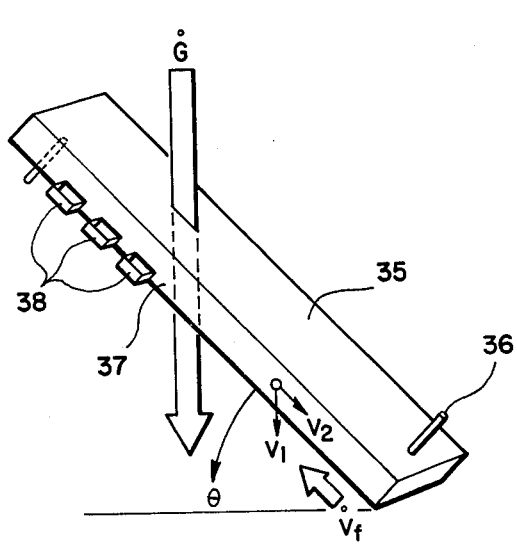
FIG. 6 depicts an elutriation embodiment of the subject steric FFF device.

This embodiment is illustrated in FIG. 6 which shows a steric FFF device 35 similar to that of FIG. 2, positioned in a sloping configuration and having an inlet 36 for channel flow located at the base section of the apparatus. Channel flow, represented by vector $V_f$, is no longer perpendicular in orientation to the applied field G. Because of this tilt at some angle $\theta$, particles 27 carried along the flow channel will sediment quickly to the wall and then tend to sediment down along the length of the wall toward inlet 36. In this manner, such particles will avoid the open space of the channel and will therefore not be subjected to the diverse flows in this channel region. Instead, particles of a given size and shape will form layers of a given thickness against the wall, resulting in a more constant effective displacement velocity of the flow stream.

With the introduction of uniformity in flow displacement with respect to a specific class of particle sizes, very slight shifts in over all flow rates will serve to shift the net velocity of a given particle type from positive to negative. In this way, a programmed flow would elute particles of gradually increasing size which could be collected as uniform fractions. The same results could be achieved by a programmed tilting of the channel axis through a series of changing angles $\theta$ toward the horizontal axis.

In such steric elutriation systems, the mean upward flow velocity acting to lift each particle is proportional to the effective diameter of that particle. The upward force is proportional to the product of the mean upward flow velocity and the particle diameter, and is thus proportional to the particle diameter squared. As in normal elutriation, the sedimentation force is proportional to the cube of the particle diameter. Therefore, in steric elutriation a doubling in the particle size means that the sedimentation force will increase by a factor of eight and the "lift" force will increase by a factor of four. In normal elutriation the lift force will increase only by a factor of two, thus giving a bigger differential between the forces of normal elutriation systems. This benefit of normal elutriation, however, is overcome by the preferred uniformity of flow displacement which is obtained in steric elutriation.

As an example of the programmed elution of particles of different size by means of the steric elutriation method, consider a particle mixture of two distinct sizes. During operation of the system, the largest particles will be inclined to sediment downward against channel flow. If the similar particles are exactly at equilibrium between the sedimentation force and the lift force, then the larger particles will settle rapidly, leaving the smaller particles in place along the length of the channel. By slightly increasing the flow to raise the lift force above the sedimentation force for the smaller particles, these particles will be eluted, while the larger particles are retained in the channel. When no other small particles are detected in the effluent, the flow rate can be increased to discharge the larger particles. By programming flow velocity increase or the axis of tilt in small incremental changes, particles of different sizes could be selectively eluted while the larger particles are retained and gradually carried by classes of size upward along the flow channel.

As a slight modification of the steric elutriation system, tapered channels in width or thickness could be utilized in order to cause a continuous variation in the magnitude of the lifting flow force. By this method, particles of different sizes could be brought into different equilibrium positions, permitting stationary bands of separated particles to collect along the length of the channel. After the equilibrium conditions are established, the channel could be tilted slightly toward one edge 37, collecting the particles in pockets or collection ports 38 for subsequent analysis.

This same concept of steric elutriation can be adapted for application in a centrifuge, where field of greater strength may be applied. The value of such methods would be directed to very small particles which require extremely large fields in order to obtain the imposition of the particles at the opposing wall surface. Utilizing this method, fluid types could be extended to gases as well as liquids and could be operated under laminar or turbulent flow conditions, depending upon the size of the particles.

Figure 7:
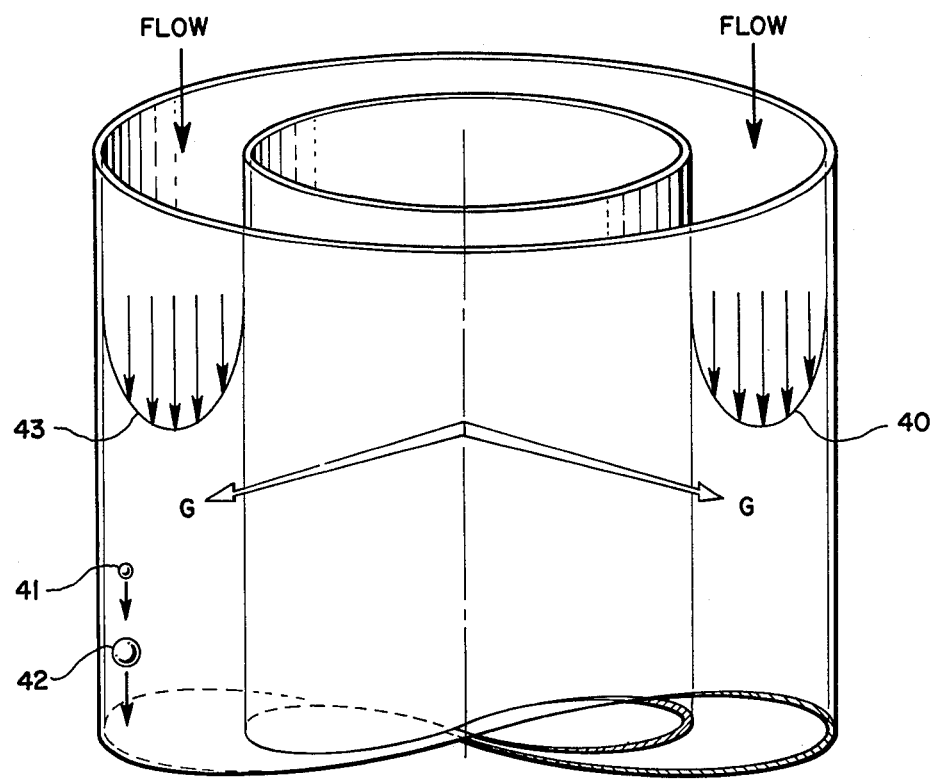
FIG. 7 graphically illustrates an annular steric-FFF system.

It will be apparent to one skilled in the art that numerous variations from the method and apparatus disclosed herein are possible. These include not only variations in force fields such as the suggested centrifugal application, but likewise include variations in geometric configurations of channel structure. FIG. 7, for example, depicts annular flow channel 40 having a field gradient applied radially outward from the annular axis. The particles 41 and 42 are advanced along the channel in accordance with their interaction with different flow rates 43 of the stream. The displacement of the larger particle 42 is in advance of the smaller particle 41 in view of the steric FFF effect.

It is to be understood, therefore, that the present disclosure is only by way of example and that substantial variations are possible from the structure and method disclosed herein without departing from the scope of the hereinafter claimed subject matter.

I claim:

1. In a field-flow fractionation system including a flow channel formed between opposing surfaces of channel walls and a force field disposed across said channel with a field gradient in a direction of one of said wall surfaces which operates as a restraining wall, the improvement comprising a method for steric field-flow fractionation including the step of applying a force field in sufficient relative strength with respect to particles contained within said channel to cause migration of a given class of said particles toward and against said restraining wall such that the mean Brownian displacement of said particles from the restraining wall is approximately equal to or less than the mean radius of said class of particles.

2. In a field-flow fractionation system including a flow channel formed between opposing surfaces of channel walls and a force field disposed across said channel with a field gradient in a direction of one of said wall surfaces which operates as a restraining wall, the improvement comprising a method for steric field-flow fractionation including the step of applying said force field in sufficient relative strength with respect to particles contained within said channel to cause formation of a layer of a given class of said particles against said restraining wall, layer thickness being controlled by the steric exclusion of particles from the space occupied by said restraining wall.

3. In a field-flow fractionation system including a flow channel formed between opposing surfaces of channel walls and a force field disposed across said channel with a field gradient in a direction of one of said wall surfaces which operates as a restraining wall, the improvement comprising a method for steric field-flow fractionation including the step of applying a force field having sufficient strength relative to particle size to maintain substantially all particles of a given class in layers in contact or near contact with said restraining wall such that the distance of the particles from the restraining wall is a function of said particle radii.

4. A method for steric field-flow fractionation as defined in claims 1, 2, or 3, wherein values for channel width (w) representing the distance between the opposing channel walls are selected from values within the approximate range $120 > w/r > 12$ in which (r) represents particle radius of a given class of particles to be subjected to fractionation therein.

5. A method for steric field-flow fractionation as defined in claims 1, 2, or 3, wherein the channel width (w) is selected from the approximate range 500 micrometers $> w >$ 50 micrometers.

6. A method for steric field-flow fractionation as defined in claims 1, 2, or 3, wherein channel width (w), field selection and stream flow rate are selected for fractionation of particles having radii within the approximate range of 1–100 micrometers.

7. A method for steric field-flow fractionation as defined in claims 1, 2, or 3, wherein the force field is selected from the group of forces consisting of gravitational, electrical, electromagnetic, photophoretic centrifugal, and fluid cross-flow.

8. A method for steric field-flow fractionation as defined in claims 1, 2, or 3, further comprising the step of elevating said channel at one end to form an angle $\theta$ with respect to horizontal, said channel having an inlet at a lower end thereof to permit upward flow of a carrier stream along the flow channel, thereby subjecting particles contained therein to a sedimentation force component opposing the upward force exerted by the flow of the carrier stream.

9. A method for steric field-flow fractionation as defined in claim 8 further comprising the step of varying the angle $\theta$ during a single fractionation procedure to thereby change the value of the opposing sedimentation force component with respect to the upward extended by the flow stream.

10. A method for steric field-flow fractionation as defined in claim 9, wherein the variation of angle $\theta$ is programmed to selectively control particle movement through the flow channel.

11. A method for steric field-flow fractionation as defined in claim 9, wherein the variation of mean flow velocity if programmed to selectively control particle movement through the flow channel.

12. A method for steric field-flow fractionation as defined in claim 8 further comprising the step of varying mean flow velocity during a single fractionation procedure to thereby change the value of the opposing sedimentation force component with respect to the upward force extended by the flow stream.

13. A method for steric field-flow fractionation as defined in claim 8 further comprising the step of forming a plurality of particle collection pockets extending laterally of the flow chanel such that particles entrained in the flow stream adjacent thereto would be captured when the channel is rotated about its longitudinal axis to cause sedimentation forces to draw the particles into the pockets.

14. A method as defined in claim 1 wherein the flow channel is annular in configuration, said force being applied radially with respect to a longitudinal axis of said annular channel.

15. A method as defined in claim 14, wherein the force extends radially outward.

* * * * *